(12) United States Patent
Wardoyo et al.

(10) Patent No.: US 9,950,998 B2
(45) Date of Patent: Apr. 24, 2018

(54) SULPHATED CHELATING AGENT

(71) Applicants: Haryanto Wardoyo, Banten (ID);
Bobby Hadipraja, Jakarta (ID)

(72) Inventors: Haryanto Wardoyo, Banten (ID);
Bobby Hadipraja, Jakarta (ID)

( * ) Notice: Subject to any disclaimer, the term of this patent is extended or adjusted under 35 U.S.C. 154(b) by 257 days.

(21) Appl. No.: 14/649,372

(22) PCT Filed: Nov. 22, 2013

(86) PCT No.: PCT/ID2013/000009
§ 371 (c)(1),
(2) Date: Jun. 3, 2015

(87) PCT Pub. No.: WO2014/097284
PCT Pub. Date: Jun. 26, 2014

(65) Prior Publication Data
US 2015/0315135 A1    Nov. 5, 2015

(30) Foreign Application Priority Data

Dec. 18, 2012 (ID) .................... P00201201174

(51) Int. Cl.
| | |
|---|---|
| C07C 305/04 | (2006.01) |
| C07C 303/24 | (2006.01) |
| C12N 1/06 | (2006.01) |
| C07C 305/10 | (2006.01) |

(52) U.S. Cl.
CPC .......... *C07C 305/04* (2013.01); *C07C 303/24* (2013.01); *C07C 305/10* (2013.01); *C12N 1/06* (2013.01)

(58) Field of Classification Search
CPC ... C07C 303/24; C07C 305/04; C07C 305/10; C12N 1/06
See application file for complete search history.

(56) References Cited

U.S. PATENT DOCUMENTS

2008/0227987 A1    9/2008    Mykola et al.

FOREIGN PATENT DOCUMENTS

| JP | 2003-215766 | * | 7/2003 |
|---|---|---|---|
| WO | WO 2002081487 A1 | | 10/2002 |

OTHER PUBLICATIONS

Davies et al., "The Involvement of Cell-to-Cell Signals in the Development of a Bacterial Biofilm," Science, vol. 280, No. 5361, Apr. 10, 1998, pp. 295-298.*
Kurz, "Effects of Micellization on the Kinetics of the hydrolysis of monoalkyl sulfates," J. Phys. Chem., 1962, 66(11), 2239-2246.*
English translation of JP2003-215766, Jul. 2003, pp. 1-66.*
Peter Claesson, Ueber Die Aetherschwefelsauren Der Mehrsaurigen Alkohole Und Der Kohlehydrate Nebst Einigen Bemerkungen Uber Die Constitution Der Letzteren, Journal Fuer Praktische Chemie, 1879, pp. 1-34, vol. 19, No. 2, Verlag GmbH & Co. KGaA, Weinheim.
Krems et al, The Reaction of Lauric Acid Esters with Sulfuric Acid, Journal of the American Chemical Society, 1959, pp. 1620-1627, vol. 81, ACS Publications, United States.
International Search Report and Written Opinion for International Application No. PCT/ID2013/000009, Applicant, Wardoyo et al.

* cited by examiner

*Primary Examiner* — Pancham Bakshi
*Assistant Examiner* — Mark R Luderer
(74) *Attorney, Agent, or Firm* — Richards Patent Law P.C.

(57) ABSTRACT

This invention refer to a series of substances according to formula I:

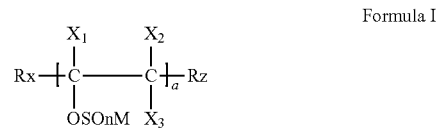

Formula I

The substances according to formula I above, known as sulphate chelating agent have the ability to enlarge/loosen simple cell membrane nor common organic membrane and its synthesis process. Furthermore, these invented substances have the potential as the biocides raw material, with very low toxicity into mammal. These features make the substances of this invention become very useful on many applications.

10 Claims, 5 Drawing Sheets

SULPHATED CHELATING AGENT

CROSS-REFERENCE TO RELATED APPLICATIONS

This application incorporates by reference and claims priority to Indonesian App. No. P 00 2012 01174, filed on Dec. 18, 2012, and PCT App. No. PCT/ID2013/000009, filed on Nov. 22, 2013.

FIELD OF THE INVENTION

This invention is related to the Sulphate chelating agents that have the capability to enlarge the membrane porosity of simple microorganism cell and its synthesis process.

BACKGROUND OF THE INVENTION

Many types of chelating agents are commonly known and have been applied in various industry. Chelating agent are chemicals contain donor atoms that have the capability to bind metallic atoms in coordinative complex bound that turn into cyclic structural substances known as chelating complex or in its simple term: a chelat. The chelation technology was developed from some naturally occurred chemicals that contain naturally or purposely added metallic ions. The use of chelating agent might give a way to control or manipulate the metallic ions in the system to perform the expected effect. The chelating complex substances formed from the interaction of some metallic ion with some chelating agent use to have significantly different characteristics/properties either from its original ions or the chelating agent itself. Therefore its characteristics or properties could be modified.

Therefore, the chelating agents are the very effective substances in the formation of the complex substances with the metallic cations and also with the organic salts in order to prevent them act as simple hydrated cations. Common example of chelating agent is Ethylene Di Amine Tetra Acetic acid (EDTA) (1) and its derivatives that will form the complex substances with most of $M^{2+}$ and $M^{3+}$ types of cations.

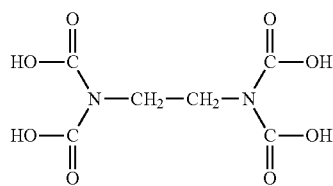

EDTA

It has been known also that gluconic acid and some others hydroxide acid perform similar properties.

There are many features of the chelating reaction that become the basic of chelating agents various applications.

The first, chelation provide a mechanism to control the concentration of the free metallic ions via dissociation equilibrium between chelating agent and the said metallic ions. The related application as the sequestration process that reduces several properties of some metal without eliminate it from the existing system or phase, solubilization is a process that elaborate undissolved component phase become soluble in the said medium, and daparing, a condition where the addition or removal of several metallic ions result insignificance change of the said ionic concentration inside the solution which totally depending on the accurate control of the chelating agent concentration.

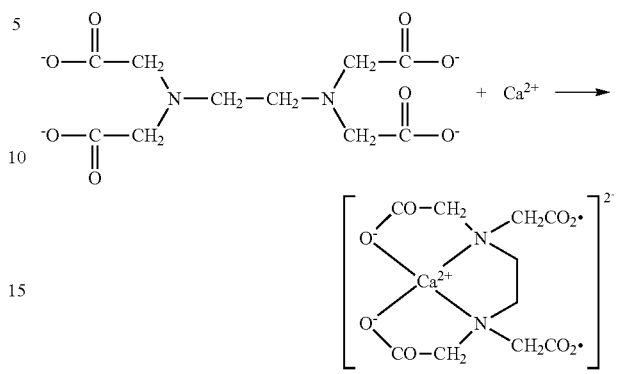

All of the above features and properties have been chemically applied in industry.

For example, the sequestration of the metallic ions could be used to control the water hardness. Then solubilization is used to dissolve the boiler scale, heat exchange equipment scale and the hard scale in the pipe.

In the mining industry, solubilization utilizes chelating agents to extract the metal from the metal ores, also to be used to clean the contaminated area.

Daparing with the chelating agents find its use to supply the metallic ions micro nutrient for the biological growth at very low stabilized concentration.

Secondly, on some applications as the chelating ligand catalyst which really has the catalytic activity dan has been applied as catalyst on the unsymmetrical pharmaceutical substances synthesis.

Finally, chelating agents have also been used for human medication. For example, the removal/cleaning with the chelating agent with its chelation termination, including the curing on the lead (Pb) poisoning and other metals with EDTA (Ethylene Di Amine Tetra Acetic acid) where lead almostly chelated to EDTA, therefore could be removed from the system.

In the publication by H. HAQUE AND A. D. RUSSELL "Effect of Chelating Agents on the Susceptibility of Some Strains of Gram-Negative Bacteria to Some Antibacterial Agents", ANTIMICROBIAL AGENTS AND CHEMOTHERAPY, August 1974, page. 200-206, explain that some chelating agents improve the activity of beta-lactam in the bacterial inhibition of *P. aeruginosa* strain through the metallic removal from the nutrient medium and some chelating agent could increase the bacterial sensitivity against some antibiotics.

In the other journal published by Kaur P, Vadehra D V., "Effect of certain chelating agents on the antibacterial action of silver nitrate." J Hyg Epidemiol Microbiol Immunol. 1988; 32(3):299-306, explain that EDTA and EGTA when applied together with $AgNO_3$ significantly increase the antibacterial action against *Staphylococcus aureus*, where EDTA and EGTA also increase the sensitivity of *Staphylococcus aureus* bacteria that is resistant against $AgNO_3$.

In the publication by A. Hinton Jr. and K. D. Ingram, "Comparison of the Antibacterial Activity of Chelating Agents Using the Agar Diffusion Method" International Journal of Poultry Science 9 (11): 1023-1026, 2010 explain that the addition of EDTA chelating agent for the cleaning agent formulation in the poultry treatment could improve the cleaning capability that has the antimicrobial activity helping to reduce poultry corpses contamination.

But until now, there is no publication describing that EDTA itself alone can perform as an antibacterial agent, due to the fact that chelating agents in some cases have the ability to influence simple cell membranes or other organic membranes.

In the US 2003/0055007 patent publication, A1 was disclosing about some lignin sulphonate substance that has the antiviral activity against HIV and also act as an antibacterial agent, but there was no further explanation about the inhibition mechanism of the said substances as the antiviral and antibacterial agent.

Therefore, it needs the development of new chelating agents and its derivatives that are non toxic or less toxic and induce no negative or less negative effect into environment, these features will significantly increase the application of the said chelating agents.

Unexpectedly, the inventor has discover such a new chelating agent that act alone as antibacterial agent. The inventor has invent a series of sulphate chelating agents that have the antibacterial activity by enlarging the cell membranes porosity of simple cells and the other organic membranes. The membrane porosity enlargement mechanism for simple cell or other organic membranes occurred due to the reaction of the sulphate groups of some sulphate chelating agent with the hydroxyl group (OH$^-$) or ammine group (NH$_2^-$) in the peptide bound of modular bound structural of a protein or modular bound structural of a peptidoglycan and their similarities as the main ingredient of the simple cell wall membranes or other organic membranes.

BRIEF DESCRIPTION OF THE INVENTION

Moreover, these invented substances have the capability as common chelating agent or substances that capable to open/enlarge the membrane porosity of either simple cell membrane wall or another organic membranes, also have the potential biocidal property, and it has been discovered that the said substances have a very low toxicity against mammal and also easy to be degraded in the environment. All these features put the said substances become very useful in many applications.

In one embodiment, the present invention provides a chelating agent of formula I

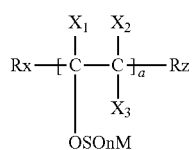

Formula I wherein:
X$_1$, X$_2$, X$_3$, are selected from: Hydrogen, hydroxy, halide, sulphite, sulphate, sulphonate, phosphorus derivatives, nitrogen derivatives, where X$_1$, X$_2$, X$_3$, could be similar or different atoms, molecules or groups.
Rx, Rz are selected from: Hydrogen, hydroxy, halide, alkyl C$_{1-20}$, alkylen C$_{1-20}$, alkyl alcohol C$_{1-20}$, aliphatic or branched substituted or non substituted, aryl, cycloalkyl substituted or non substituted, sulphite, sulphate, sulphonate, phosphorus derivatives, nitrogen derivatives.
M: are Hydrogen, or group I, group II, transition group cation that are pharmaceutically acceptable.
n: integer from 0-3
a: integer
and/or its isomer, enantiomer, stereotiomer, salt, solvate, hydrate In other preferred embodiment, this invention provide some substances selected from:
Tetra Hydroxy Ethyl Di Sulphate
Tetra Hydroxy Buthyl 1,2,3,4 Tetra Sulphate
Tri Hydroxy Isobuthyl 1,3,4-Tri Sulphate
Tetra Hydroxy Isoamyl 1,3,4,5-Tetra Sulphate
Ethyl hexa sulphate acid In the further embodiment, the preferred substances is where M is Natrium.

In the further embodiment, including its isomer, enantiomer, stereotiomer, salt, solvate, hydrate of Formula I.

In the further embodiment, the preferred substances are:
Tetra Hydroxy Ethyl Di Sulphate Di Natrium
Tetra Hydroxy Buthyl 1,2,3,4 Tetra Sulphate Tetra Natrium
Tri Hydroxy Isobuthyl 1,3,4-Tri Sulphate Tri Natrium
   Tetra Hydroxy Isoamyl 1,3,4,5-Tetra Sulphate Tetra Natrium
Ethyl Hexa Sulphate-Hexa Sodium (EHS-6Na)

In such invention embodiment provides some sulphate chelating agent represent by the above Formula I that has antibacterial activity by enlarging the membrane porosity of simple cells or another organic membranes. The membrane porosity enlargement mechanism for simple cell or other organic membranes occurred due to the reaction of the sulphate groups of some sulphate chelating agent with the hydroxyl group (OH$^-$) or ammine group (NH$_2^-$) in the peptide bound of modular bound structural of a protein or modular bound structural of a peptidoglycan and their similarities as the main ingredient of the simple cell wall membranes or other organic membranes.

In another embodiment, this invention provide some series sulphate chelating agents represent by the above Formula I that can be used as biocide.

Further embodiment of this invention is providing the synthesis process of the said sulphate chelating agent represent by Formula I,

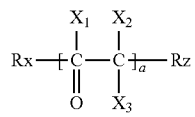

the method including reacting at least one of sulphuric acid (H$_2$SO$_4$) or sulphonic acid (H$_2$SO$_3$) and/or sulfur triokside (SO$_3$) or sulfur diokside (SO$_2$) as it is and/or might be following by polymerization to get the desired length of polymer chain with a compound which is selected from formaldehyde, acetaldehyde, formic acid, acetic acid, and oxalic acid to obtain a hydroxyl intermediate, followed by replacing the hydroxyl group of the intermediate such that X1 and X2 in Formula I are the same or different and are selected from hydroxyl and/or sulphate.

In the preferred embodiment of this invention, the said new substances I can form a complex substance with metal.

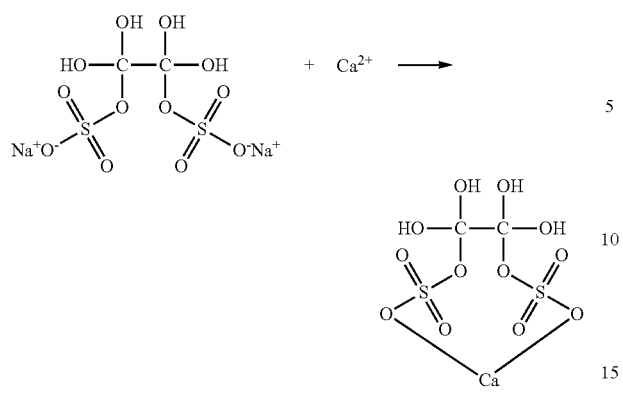

In the further aspect of this invention describing the method of membrane porosity enlargement of simple cells or another organic membranes with some effective amount of this invention.

In the preferred embodiment of this invention, the new substances of this invention to be discovered have the capability to modify membrane of simple cells or organic membranes by mean enlarging significantly the membrane porosity. By not theoretically fully supported, it is postulated due to sulphate group electronegativity of this sulphate chelating agents will tense the hydroxy-hydroxy bound of peptidoglycan and/or hydroxy-ammine bound of protein that compose cell membranes or organic membranes. The capability of these said substances are proven by mean of opening/enlarging membrane porosity of some microorganisms simple cell, such as: bacteria cell, algae, fungi, and similar with some concentration level worked on the membrane modification mechanism from semi permeable into permeable membrane therefore it is become possible for another ligand insertion into target microorganism and/or simple cell; also possible that the microrganism cell wall membranes become totally permeable result on the microorganism death due to cell internal lysis or dormant/latent condition of the target microorganism. It is postulated that this said mechanism works for almost all of microorganism having cell membranes.

DETAIL DESCRIPTION OF THE INVENTION

Figure 1:
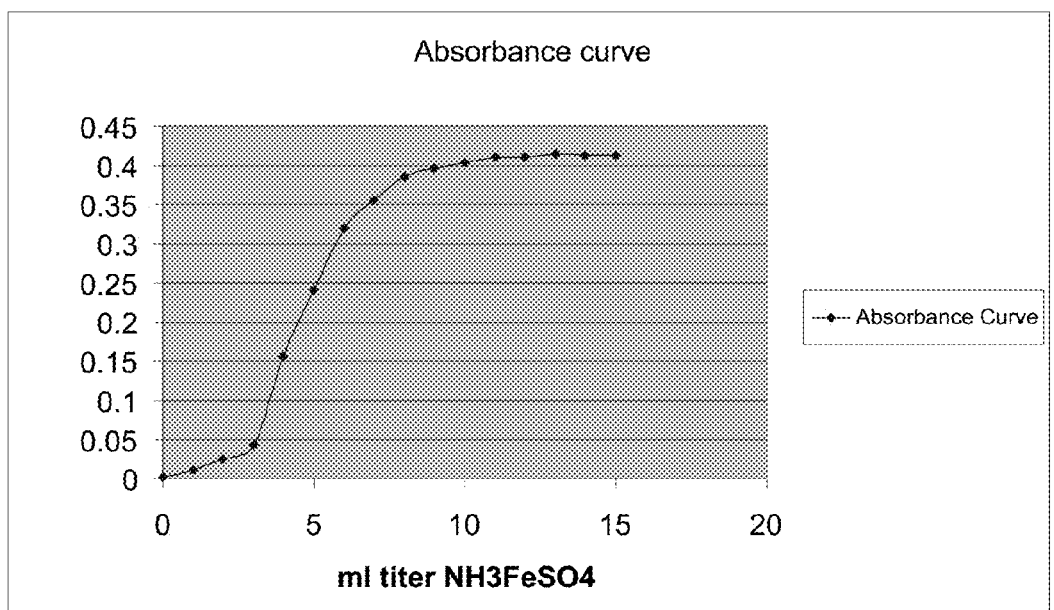
FIG. 1: Describe the absorbance curve Menggambarkan kurva absorbansi Tetra Hydroxy Ethyl Di Sulphate Di Natrium (THES) against $NH_3FeSO_4$ volume at pH 7.
Figure 2A:
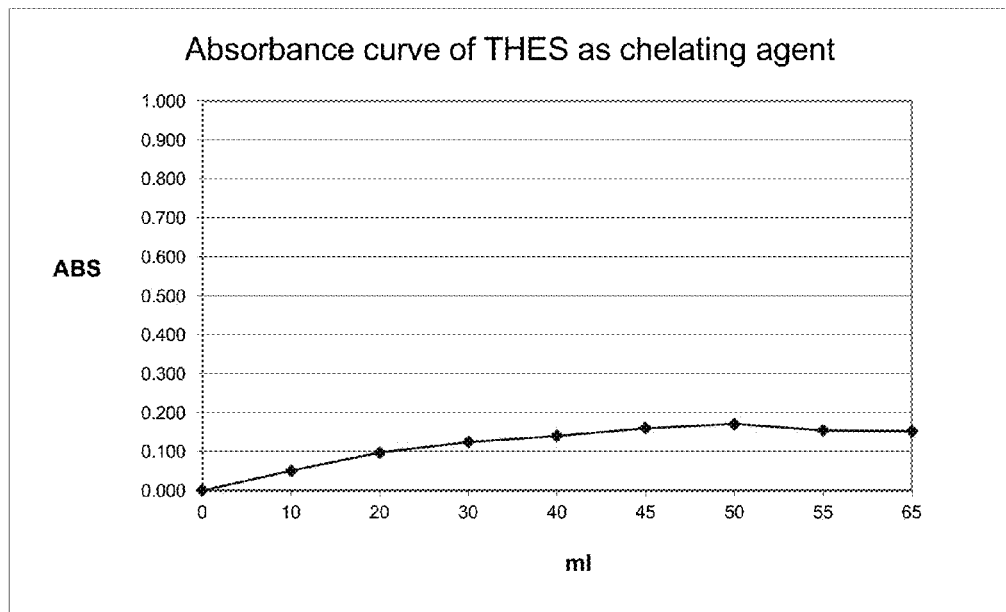
FIGS. 2a and 2b: are the titration curves show the comparation of chelating capability between THES and EDTA, where it needs less THES concentration in comparation to EDTA.
Figure 2B:
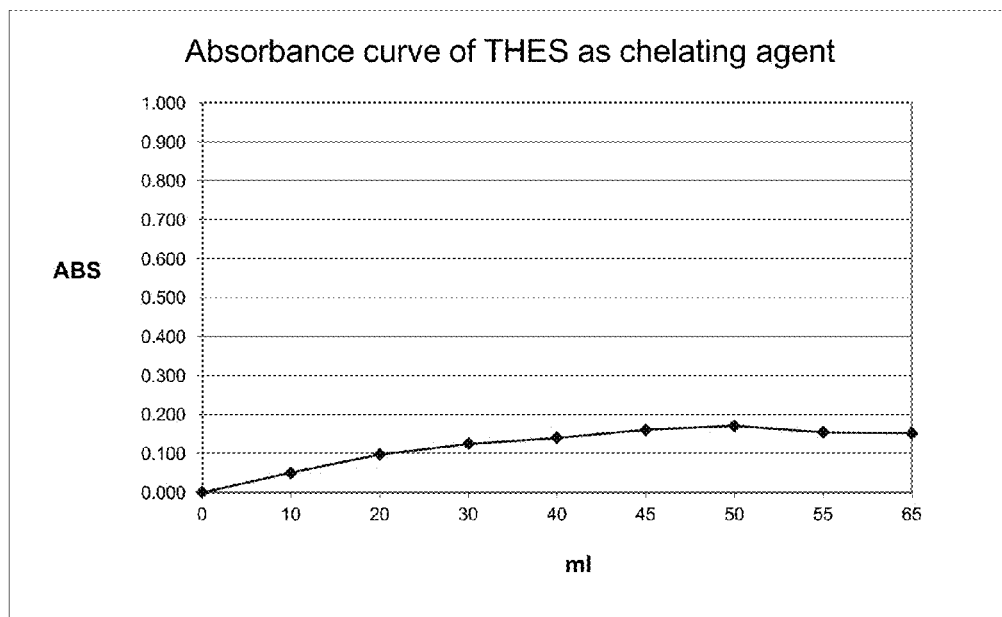
Figure 3:
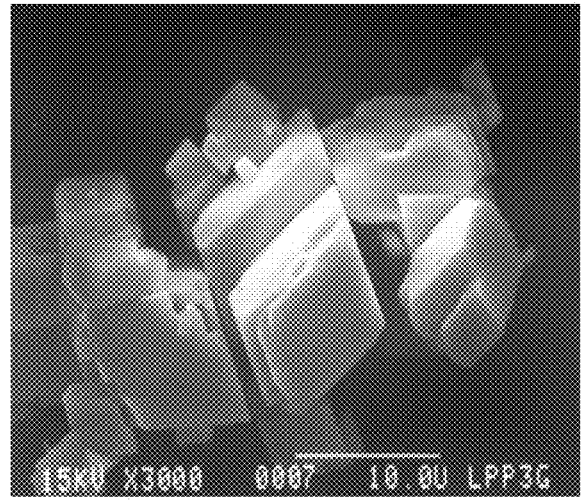
FIG. 3: SEM pictures result of pure $CaCO_3$ crystals with its rhombus structure and $CaCO_3$ crystals after chelated with Tetra Hydroksy Ethyl Di Sulphate Di Natrium (THES) at pH 7.
Figure 3:
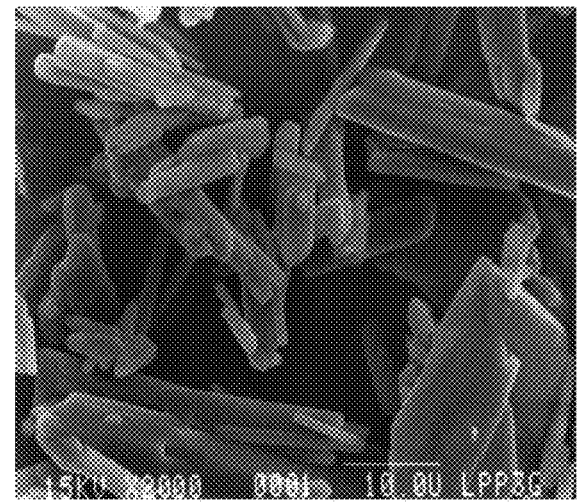
Figure 4:
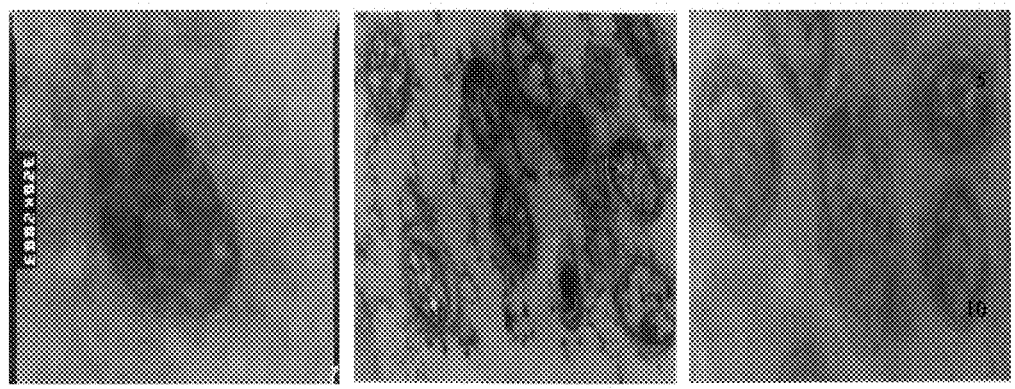
FIG. 4: Transversal section of *Staphylococcus aerus* single cell (×35,000), from left to right: Normal cell, in contact with 0.05% THES, in contact with 1% THES (tetra hydroxy ethyl di sulphate) at pH 7.
Figure 5:
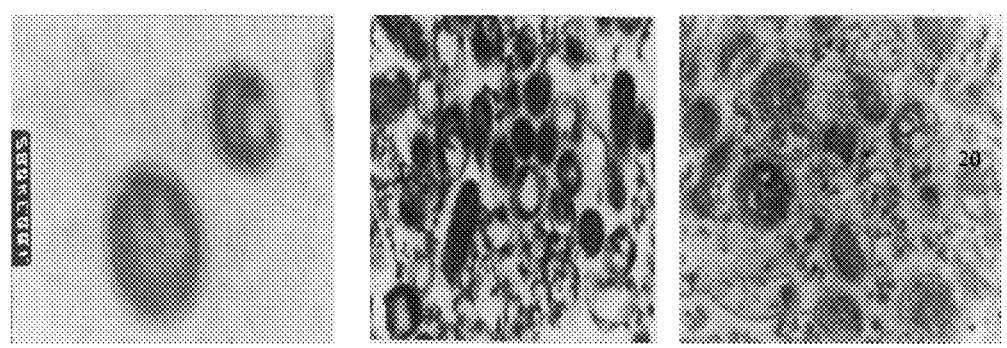
FIG. 5: Transversal section of *E. Colli* single cell (×25,000), from left to right: Normal cell, in contact with 0.05% THES, in contact with 1% THES (tetra hydroxy ethyl di sulphate) at pH 7.
Figure 6:
FIG. 6: Outer view of *Staphylococcus aerus* cell wall/membranes, from left to right: Normal cell, in contact with 1% THES (tetra hydroxy ethyl di sulphate) at pH 7.
Figure 6:
Figure 7:
FIG. 7: Outer view of *E. Colli*, cell wall/membranes, from left to right: Normal cell, in contact with 1% THES (tetra hydroxy ethyl di sulphate) at pH 7.
Figure 7:

In such embodiment of substances have the formula

Formula I

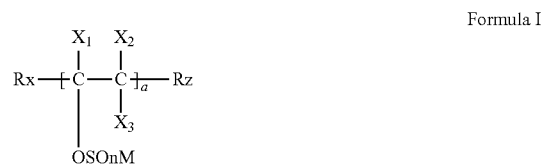

wherein:

$X_1$, $X_2$, $X_3$, are selected from: Hydrogen, hydroxy, halide, sulphite, sulphate, sulphonate, phosphorus derivatives, nitrogen derivatives, where $X_1$, $X_2$, $X_3$, could be similar or different atoms, molecules or groups.

Rx, Rz are selected from: Hydrogen, hydroxy, halide, alkyl $C_{1-20}$, alkylene $C_{1-20}$, alkyl alcohol $C_{1-20}$, aliphatic or branched substituted or unsubstituted, aryl, cycloalkyl substituted or unsubstituted, sulphite, sulphate, sulphonate, phosphorus derivatives, nitrogen derivatives.

M: are Hydrogen, or group I, group II, transition group cation that are pharmaceutically acceptable.

n: integer from 0-3 a: integer and/or its isomer, enantiomer, stereotiomer, salt, solvate, hydrate that are pharmaceutically acceptable.

In the other preferred embodiment of substances derived from Formula I where M is hydrogen.

In the most preferred embodiment of substance is

Tetra Hydroxy Ethyl Di Sulphate

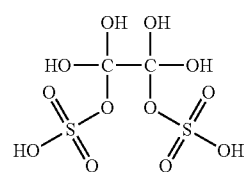

Tetra Hydroxy Buthyl 1,2,3,4 Tetra Sulphate

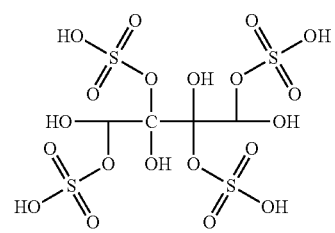 [SMILES: O=S(=O)(O)OC(O)C(O)(OS(=O)(=O)O)C(O)(OS(=O)(=O)O)C(O)OS(=O)(=O)O]

Tri Hydroxy Isobuthyl 1,3,4-Tri Sulphate

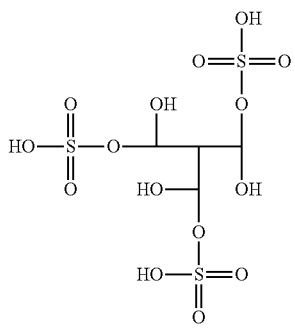

Tetra Hydroxy Isoamyl 1,3,4,5-Tetra Sulphate

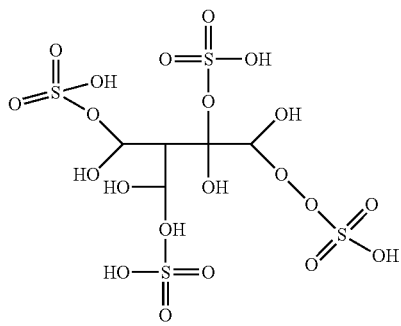 [SMILES: O=S(=O)(O)OOC(O)C(O)(OS(=O)(=O)O)C(C(O)OS(=O)(=O)O)C(O)OS(=O)(=O)O]

Ethyl Hexa Sulphate acid (EHS)

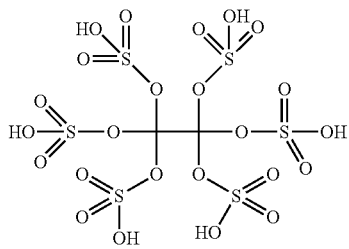 [SMILES: O=S(=O)(O)OC(OS(=O)(=O)O)(OS(=O)(=O)O)C(OS(=O)(=O)O)(OS(=O)(=O)O)OS(=O)(=O)O]

and/or its isomer, enantiomer, stereotiomer, salt, solvate, hydrate that are pharmaceutically accepted.

In the other preferred embodiment of such substances from Formula I, where M is Natrium.

In the preferred embodiment of the above substances are

Tetra Hydroxy Ethyl Di Sulphate Di Natrium

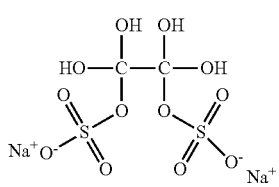 [SMILES: [Na+] ; O=S(=O)([O-])OC(O)(O)C(O)(O)OS(=O)(=O)[O-] ; [Na+]]

Tetra Hydroxy Buthyl 1,2,3,4 Tetra Sulphate Tetra Natrium

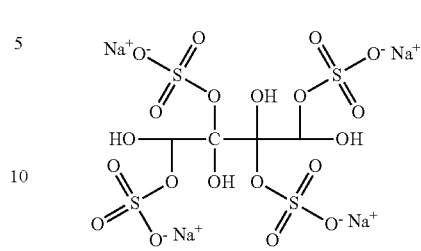

Tri Hydroxy Isobuthyl 1,3,4-Tri Sulphate Tri Natrium

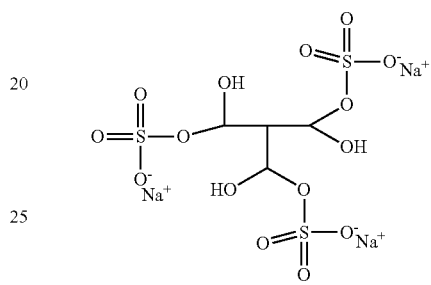

Tetra Hidroxy Isoamyl 1,3,4,5-Tetra Sulphate Tetra Natrium.

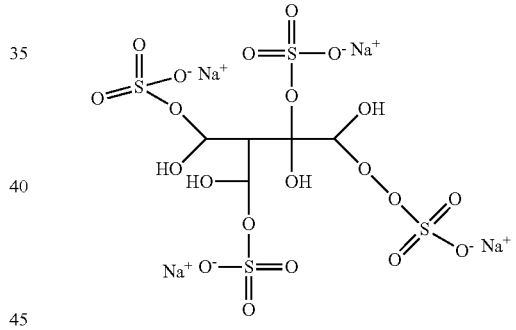

Ethyl Hexa Sulphate-Hexa Natrium (EHS-6Na)

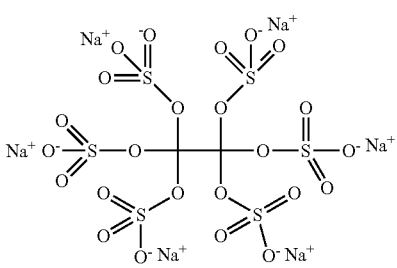

and/or its isomer, enantiomer, stereotiomer, salt, solvate, hydrate that are pharmaceutically accepted.

Furthermore, the formed alkyl sulphate substances derived from formula I are still enabled to be polymerized to form longer chain.

In the preferred embodiment of this invention covers breaking or loosening the hydroxyl-hydroxyl bound of peptidoglycan or hydroxyl-ammine bound of protein that compose cell wall membranes or organic membranes by mean utilizing some sulphate chelating agent that result on the enlargement of the membrane porosity, therefore the membrane become permeable on both of its sides. The capability of the said substances was proven by opening/enlargement the microorganism simple cell's membrane, such as bacteria, algae, fungi, virus, etc with some concentration level that works on the cell wall membrane modification from semi permeable membrane into more and more permeable, therefore it becomes possible to insert another ligands inside the microorganism or the cell wall membrane become totally permeable that result on the microorganism death and/or microorganism dormant condition. It is postulated the said mechanism works for all types of microorganism that has cell membrane.

Definition

The following terms are used throughout the specification and have the following meanings unless otherwise specified:

"Alkyl" means carbon atom chains having the designated number of carbon atoms which can be either straight chain or branched. Examples of alkyl include but are not limited to, methyl, ethyl, propyl, butyl, isobutyl, and the like.

"Alkenyl" means carbon atom chains having the designated number of carbon atoms which can be either straight chain or branched and which contain at least one double bond. The alkenyl compounds may have more than one such double bond and the orientation about each double bond is independently either cis or trans. Examples of alkenyl include, but are not limited to ethenyl, propenyl, butenyl, isobutenyl, pentenyl, hexenyl and the like.

"Alkynyl" means carbon atom chains having the designated number of carbon atoms which can be either straight chain or branched and which contain at least one triple bond.

As used herein the term "aryl" means single, polynucleic conjugated and fused residues of aromatic hydrocarbon or aromatic heterocyclic ring systems, examples of aryl include, but are not limited to phenyl, naphthyl, fluorenyl, pyrinyl, pyridyl, pyrollyl, and the like.

Cycloalkyl termination refers to non-aromatic aliphatic ring moiety of 3-20 mono-cyclic, bicyclic, or polycyclic carbon atoms. Cycloalkyl can be bicycloalkyl, polycycloalkyl, branched, or spiroalkyl. One or more of the rings might have one or more double bond but no such ring has fully conjugated pi-electron system. Example, without limitation, of cycloalkyl group are: cyclopropane, cyclobutane, cyclopentane, cyclopenthenyl, cyclohexane, cyclohexadiene, adamanthane, cycloheptane, cycloheptatriene, and the like.

Sulphite structure could be described with three equal resonance structures. In every resonance structure, the sulphur atom has a double bond with one oxygen atom with zero/neutral charge, and the single sulphur atom is bound into two other oxygen atoms that each has formal charge of −1. It is also found free electrons pair on Sulphur atom, therefore the predicted structure by VSEPR theory is a pyramid trigonal similar to amonia (NH3)

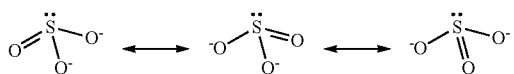

Sulphate termination refers to sulphur as the centered atom surrounded by four equal oxygen atoms in tetrahedral structure. Sulphur atom in its oxidation state +6 while the four oxygen atoms, each in its oxidation state −2. Sulphate ion carry negative charge and two of them are the alkaline conjugate of bisulphate (or hydrogen sulphate), $HSO_4^-$, as the alkaline conjugate of $H_2SO_4$, sulphuric acid.

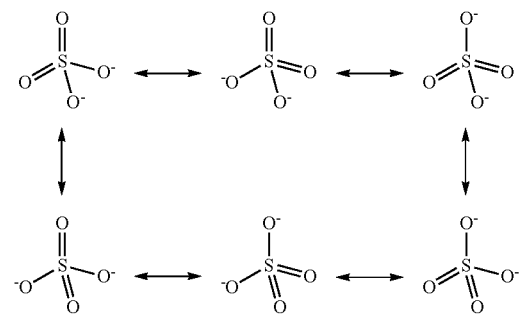

Sulphonate termination refers to an ester of sulphonic acid. An ester with the common formula $ROSO_2R'$ is a sulphonic ester. The common structures of sulphonic ester shown by the structures below:

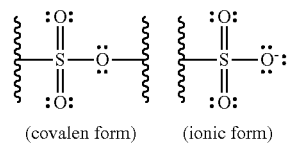 [SMILES: *OS(*)(=O)=O ; *S(=O)(=O)[O-]]

(covalen form)    (ionic form)

Nitrogen derivatives termination refers to carbon substances that contain nitrogen atom, cyclical or aliphatic, straight or branched chain, if it has cyclical structure, then it could be in fusion or non fusion form, could be aromatic or non aromatic.

Phosphorous derivatives termination refers to carbon substances that contain phosphorous atom, cyclical or aliphatic, straight or branched chain, if it has cyclical structure, then it could be in fusion or non fusion form, could be aromatic or non aromatic.

Pharmaceutically accepted salts refer to alkaline addition types of salts synthesized by adding some alkaline substances to the said substances in this invention. The common pharmaceutically accepted salts are: natrium, kalium, calcium or zink.

In the specification, the termination of substituted means that a group may be further substituted with one or more groups selected from alkyl, alkenyl, alkunyl, aryl, fluoro, chloro, bromo, hydroxyl, alkoxy, alkenyloxy, aryloxy, acyloxy, amino, alkylamino, dialkylamino, arylamino, thio, alkylthio, arylthio, cyano, nitro, acyl, amido, alkylamido, dialkylamido, carboxyl or two or more substituents may, together with the carbon atoms to which they are attached from a 5 or 6 membered aromatic or non aromatic ring containing 0, 1 or 2 heteroatoms selected from nitrogen, oxygen and sulphur.

Main selection of the preferred substances of this invention are:
 a. Tetra Hydroxy Ethyl Di Sulphate
 b. Tetra Hydroxy Ethyl Di Sulphate Di Natrium
 c. Tetra Hydroxy Buthyl 1,2,3,4 Tetra Sulphate
 d. Tetra Hydroxy Buthyl 1,2,3,4 Tetra Sulphate Tetra Natrium.
 e. Tri Hydroxy Isobuthyl 1,3,4-Tri Sulphate f. Tri Hydroxy Isobuthyl 1,3,4-Tri Sulphate Tri Natrium
g. Tetra Hydroxy Isoamyl 1,3,4,5-Tetra Sulphate
h. Tetra Hydroxy Isoamyl 1,3,4,5-Tetra Sulphate Tetra Natrium
i. Ethyl hexa sulphate acid
j. Ethyl hexa sulphate-hexa sodium (EHS-6Na)

Synthesis of the Substances of Formula (1) or (2) are of Below:

reacting keton/aldehyde/carboxylate compound in formula III below

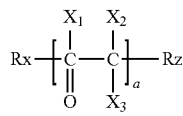

Formula III wherein:
$X_1$, $X_2$, $X_3$, are selected from: Hydrogen, hydroxy, halide, sulphite, sulphate, sulphonate, phosphorus derivatives, nitrogen derivatives, where $X_1$, $X_2$, $X_3$, could be similar or different atoms, molecules or groups.
Rx, Rz are selected from: Hydrogen, hydroxy, halide, alkyl $C_{1-20}$, alkylen $C_{1-20}$, alkyl alcohol $C_{1-20}$, aliphatic or branched substituted or unsubstituted, aryl, cycloalkyl substituted or unsubstituted, sulphite, sulphate, sulphonate, phosphorus derivatives, nitrogen derivatives;
a: integer;
with sulphuric acid ($H_2SO_4$) and/or sulphonic acid ($H_2SO_3$) and/or sulphur trioxide ($SO_3$) and/or sulphur dioxide ($SO_2$),

EXAMPLES OF THE SYNTHESIS OF SOME SUBSTANCES WITHIN THIS INVENTION

Example 1: Synthesis of Tetra Hydroxy Ethyl Di Sulphate (THES)

225 g of oxalic acid crystal was diluted in 150 ml of water and the resulted slurry heated to 40-50° C. To this slurry was added dropwise 250 ml of 98% $H_2SO_4$. The rate of acid addition was controlled to ensure that the temperature of the slurry was in the range of 90-100° C. at atmospheric pressure. Upon completion of $H_2SO_4$ acid addition, the solution is still heated with agitation until the next 180 minutes with the installation of vertical pipe condenser for reflux purposes to maintain the volume of the liquid until a very clear solution is achieved.

Then the liquid temperature was raised to 90-100° C.

Evaporation of the solvent followed by crystallization result in formation of the desired substance as an off white powder with the following properties: melting point >200° C., boiling point >400° C., specific gravity=1.86, water solubility 48%.

Example 2: Synthesis of Tetra Hydroxy Ethyl Di Sulphate-Di Natrium (THES-2Na)

90 g of oxalic acid crystal was diluted in 150 ml of water and the resulted slurry heated to 40-50° C. To this slurry was added dropwise 100 ml of 98% $H_2SO_4$. The rate of acid addition was controlled to ensure that the temperature of the slurry heated with agitation until the next 180 minutes with the installation of vertical pipe condenser for reflux was in the range of 90-100° C. at atmospheric pressure. Upon completion of $H_2SO_4$ acid addition, the solution is still heated with agitation until the next 180 minutes with the installation of vertical pipe condenser for reflux purposes to maintain the volume of the liquid until a very clear solution is achieved.

To this clear solution was added dropwise a solution of 73 g NaOH flakes in 75 ml of water with the rate of addition being controlled so that the temperature of the solution remained at 50±20° C. Upon completion of addition, the temperature was adjusted slowly to ambient and the solution was held agitated in the ambient temperature for the next 60 minutes.

Evaporation of the solvent followed by crystallization result in formation of the desired substance as an off white powder with the following properties: melting point >200° C., boiling point >400° C., specific gravity=2.2, water solubility 31%.

Example 3: Synthesis of Tetra Hydroxy Butyl 1,2,3,4-Tetra Sulphate 184 g formic acid crystal was diluted in 300 ml of water and the resulted slurry heated to 40-50° C. To this slurry was added dropwise 230 ml of 98% $H_2SO_4$. The rate of acid addition was controlled to ensure that the temperature of the slurry was in the range of 90-100° C. at atmospheric pressure. Upon completion of $H_2SO_4$ acid addition, the solution is still heated with agitation for the next 60 minutes, then 8.6 gram of natrium peracetate was added as the catalyst for polymerization process with the installation of vertical pipe condenser during the next 120 minutes reflux until a very clear solution is achieved. Then the temperature was adjusted slowly to ambient and the solution was held agitated in the ambient temperature for the next 60 minutes.

Upon 60 minutes agitation completion, the condenser was released, then the solution is boiled for around 2 hours to evaporate the water until 35-40% of its original volume evaporated. The resulting solution then undergoes slow cooling into ambient temperature and cooling further into ±10° C. by ice water bath. The resulting suspension then is filtrated to separate the Tetra Hydroxy Butyl 1,2,3,4 Tetra Sulphate acid crystals, the separated crystals then oven dried at ±70-80° C. until the constant weight reached.

Example 4: Synthesis of Tetra Hidroxy Butyl 1,2,3,4-Tetra Sulphate-Tetra Natrium 184 g formic acid crystal was diluted in 300 ml of water and the resulted slurry heated to 40-50° C. To this slurry was added dropwise 230 ml of 98% $H_2SO_4$. The rate of acid addition was controlled to ensure that the temperature of the slurry was in the range of 90-100° C. at atmospheric pressure. Upon completion of $H_2SO_4$ acid addition, the solution is still heated with agitation for the next 60 minutes, then 8.6 gram of natrium peracetate was added as the catalyst for polymerization process with the installation of vertical pipe condenser during the next 120 minutes reflux until a very clear solution is achieved. To this clear solution was added dropwise a solution of 170 g NaOH flakes in 200 ml of water with the rate of addition being controlled so that the temperature of the solution remained at 50±20° C. Upon completion of addition, the temperature was adjusted slowly to ambient and the solution was held agitated in the ambient temperature for the next 60 minutes.

Upon 60 minutes agitation completion, the condenser was released, then the solution is boiled for around 2 hours to evaporate the water until 35-40% of its original volume evaporated. The resulting solution then undergoes slow cooling into ambient temperature and cooling further into ±10° C. by ice water bath. The resulting suspension then is filtrated to separate the Tetra Hydroxy Butyl 1,2,3,4 Tetra Sulphate Tetra Natrium crystals, the separated crystals then oven dried at +70-80° C. until the constant weight reached.

Example 5: Synthesis of Tri Hydroxy Isobutyl 1,2,3-Tri Sulphate 138 g formic acid crystal was diluted in 300 ml of water and the resulted slurry heated to 40-50° C. To this slurry was added dropwise 173 ml of 98% $H_2SO_4$. The rate of acid addition was controlled to ensure that the temperature of the slurry was in the range of 90-100° C. at atmospheric pressure. Upon completion of $H_2SO_4$ acid addition, the solution is still heated with agitation for the next 60 minutes, then 8.6 gram of natrium peracetate was added as the catalyst for polymerization process with the installation of vertical pipe condenser during the next 120 minutes reflux until a very clear solution is achieved. Next, prepare methanol solution of 34 g methanol 96% technical grade in 60 mL aquadess; into this solution, 43 g of Caustic soda flakes was added following by 30 minutes agitation, until the salt precipitated perfectly.

Then the said hot liquid was cooling slowly into ambient temperature while still agitated for the next 60 minutes. Separate the precipitated salt through filter to get the clear filtrate.

Upon the filtration completion, the condenser was released, then the solution is boiled for around 2 hours to evaporate the water until 35-40% of its original volume evaporated. The resulting solution then undergoes slow cooling into ambient temperature and cooling further into ±10° C. by ice water bath. The resulting suspension then is filtrated to separate the Tri Hydroxy Butyl 1,2,3 Tri Sulphate acid; the separated crystals then oven dried at ±70-80° C. until the constant weight reached.

Example 6: Synthesis of Tri Hidroxy Isobutyl 1,2,3-Tri Sulphate-3Natrium 138 g formic acid crystal was diluted in 300 ml of water and the resulted slurry heated to 40-50° C. To this slurry was added dropwise 173 ml of 98% $H_2SO_4$. The rate of acid addition was controlled to ensure that the temperature of the slurry was in the range of 90-100° C. at atmospheric pressure. Upon completion of $H_2SO_4$ acid addition, the solution is still heated with agitation for the next 60 minutes, then 8.6 gram of natrium peracetate was added as the catalyst for polymerization process with the installation of vertical pipe condenser during the next 120 minutes reflux until a very clear solution is achieved. Next, prepare methanol solution of 34 g methanol 96% technical grade in 60 mL aquadess; into this solution, 43 g of Caustic soda flakes was added following by 30 minutes agitation, until the salt precipitated perfectly.

Then the said hot liquid was cooling slowly into ambient temperature while still agitated for the next 60 minutes. Separate the precipitated salt through filter to get the clear filtrate.

To this clear solution was added dropwise a solution of 130 g NaOH flakes in 200 ml of water with the rate of addition being controlled so that the temperature of the solution remained at 50±20° C.

Upon completion, the condenser was released, then the solution is boiled for around 2 hours to evaporate the water until 35-40% of its original volume evaporated. The resulting solution then undergoes slow cooling into ambient temperature and cooling further into ±10° C. by ice water bath. The resulting suspension then is filtrated to separate the Tri Hydroxy Butyl 1,2,3 Tri Sulphate-3Natrium crystals; the separated crystals then oven dried at ±70-80° C. until the constant weight reached.

Example 7: Synthesis of Tetra Hydroxy Isoamyl 1,2,3,4 Tetra Sulphate 184 g formic acid crystal was diluted in 300 ml of water and the resulted slurry heated to 40-50° C. To this slurry was added dropwise 230 ml of 98% $H_2SO_4$. The rate of acid addition was controlled to ensure that the temperature of the slurry was in the range of 90-100° C. at atmospheric pressure. Upon completion of $H_2SO_4$ acid addition, the solution is still heated with agitation for the next 60 minutes, then 8.6 gram of natrium peracetate was added as the catalyst for polymerization process with the installation of vertical pipe condenser during the next 120 minutes reflux until a very clear solution is achieved. Next, prepare methanol solution of 34 g methanol 96% technical grade in 60 mL aquadess; into this solution, 43 g of Caustic soda flakes was added following by 30 minutes agitation, until the salt precipitated perfectly.

Then the said hot liquid was cooling slowly into ambient temperature while still agitated for the next 60 minutes. Separate the precipitated salt through filter to get the clear filtrate.

Upon the filtration completion, the condenser was released, then the solution is boiled for around 2 hours to evaporate the water until 35-40% of its original volume evaporated. The resulting solution then undergoes slow cooling into ambient temperature and cooling further into ±10° C. by ice water bath. The resulting suspension then is filtrated to separate the Tetra Hydroxy Isoamyl 1,2,3,4 Tetra Sulphate acid; the separated crystals then oven dried at ±70-80° C. until the constant weight reached.

Example 8: Synthesis of Tetra Hydroxy Isoamyl 1,2,3,4 Tetra Sulfat-4Natrium 184 g formic acid crystal was diluted in 300 ml of water and the resulted slurry heated to 40-50° C. To this slurry was added dropwise 230 ml of 98% $H_2SO_4$. The rate of acid addition was controlled to ensure that the temperature of the slurry was in the range of 90-100° C. at atmospheric pressure. Upon completion of $H_2SO_4$ acid addition, the solution is still heated with agitation for the next 60 minutes, then 8.6 gram of natrium peracetate was added as the catalyst for polymerization process with the installation of vertical pipe condenser during the next 120 minutes reflux until a very clear solution is achieved.

Next, prepare methanol solution of 34 g methanol 96% technical grade in 60 mL aquadess; into this solution, 43 g of Caustic soda flakes was added following by 30 minutes agitation, until the salt precipitated perfectly.

Then the said hot liquid was cooling slowly into ambient temperature while still agitated for the next 60 minutes. Separate the precipitated salt through filter to get the clear filtrate.

To this clear solution was added dropwise a solution of 170 g NaOH flakes in 200 ml of water with the rate of addition being controlled so that the temperature of the solution remained at 50±20° C.

Upon completion, the condenser was released, then the solution is boiled for around 2 hours to evaporate the water until 35-40% of its original volume evaporated. The resulting solution then undergoes slow cooling into ambient temperature and cooling further into ±10° C. by ice water bath. The resulting suspension then is filtrated to separate the Tetra Hydroxy Isoamyl 1,2,3,4 Tetra Sulphate-4Natrium; the separated crystals then oven dried at +70-80° C. until the constant weight reached.

Example 9: Synthesis of Ethyl Hexa Sulphate (EHS)

75 g of oxalic acid crystal was diluted in 75 ml of water and the resulted slurry heated to 40-50° C. To this slurry was added dropwise 250 ml of 98% $H_2SO_4$. The rate of acid addition was controlled to ensure that the temperature of the slurry heated with agitation until the next 180 minutes with the installation of vertical pipe condenser for reflux was in the range of 90-100° C. at atmospheric pressure. Upon completion of $H_2SO_4$ acid addition, the solution is still heated with agitation until the next 120 minutes with the installation of vertical pipe condenser for reflux purposes to maintain the volume of the liquid until a very clear solution is achieved; then the vertical pipe condenser was released, the resulting solution is still heated with another 30 minutes agitation to ensure complete and homogenous sulphatation reaction.

Then the liquid temperature was raised to 100-105° C. Evaporate half of the solvent volume followed by crystallization result in formation of the desired substance as an off white powder with the following properties: melting point >210° C., boiling point >400° C., specific gravity=1.87, water solubility 48% and very higroscopic.

Example 10: Synthesis of Ethyl Hexa Sulphate-Hexa Natrium (EHS-6Na)

75 g of oxalic acid crystal was diluted in 75 ml of water and the resulted slurry heated to 40-50° C. To this slurry was added dropwise 250 ml of 98% $H_2SO_4$. The rate of acid addition was controlled to ensure that the temperature of the slurry heated with agitation until the next 180 minutes with the installation of vertical pipe condenser for reflux was in the range of 90-100° C. at atmospheric pressure. Upon completion of $H_2SO_4$ acid addition, the solution is still heated with agitation until the next 120 minutes with the installation of vertical pipe condenser for reflux purposes to maintain the volume of the liquid until a very clear solution is achieved; then to this clear solution was added dropwise a solution of 185 g NaOH flakes in 190 ml of water with the rate of addition being controlled so that the temperature of the solution remained at 50±20° C. within one hours time. Then the vertical pipe condenser was released, the resulting solution is still heated with another 30 minutes agitation to ensure complete and homogenous neutralization reaction.

Then the liquid temperature was raised to 100-105° C. Evaporate half of the solvent volume followed by crystallization result in formation of the desired substance as an off white powder with the following properties: melting point >360° C., boiling point >400° C., specific gravity=2.21, water solubility 29% and higroscopic.

Analytical Method:
Analytical Method to Determine Tetra Hydroxy Ethyl Di Sulphate-Di Natrium (THES-2Na), Utilizing Iron's Chelating Agent Test Principle:
Active matter of Tetra Hydroxy Ethyl Di Sulphate-Di Natrium (THES-2Na) was determined by chelating reaction of residual metallic ion with several anionic surfactants that prevent this anionic surfactants dissolved in the solution result in the turbid solution measured by its turbidity and/or absorbance spectrophotometer.

Materials and Equipments:
Materials:
Reagent grade $NH_3FeSO_4.2H_2O$, reagent grade Natrium Laurier Ethoxylate sulphate (Na-SLES), Caustic Soda flakes, aquadess.

Equipments:
Visible Spectrofotometer, cuvet, erlen meyer, beaker glass, pipete, scale weight, magnetic stirrer.

Method:
I. Absorbance:
1) Add 2 gr Na-SLES into 100 cc aquades, stir with magnetic stirrer for 15 minutes until clear solution (1) reached.
2) Add on 1.0 cc of tested chelating agent (THES-2Na), stir with magnetic stirrer for 15 minutes until homogenous solution (2).
3) Adjust the pH of the solution above into 7 with Caustic Soda flakes.
4) Prepare 50 cc 0.1 M NH3FeSO4 solution in the 100 cc beaker glass.
5) Fill the cuvet with the solution (2), record the absorbance at 450 nm.
6) Titration starts with the addition of 1.0 cc 0.1 M NH3FeSO4 solution into solution (2), stir with magnetic stirrer for 2 minutes until homogenous solution (3).
7) Fill the cuvet with the solution (3), record the absorbance at 450 nm.
8) Repeat step 5 and 6 until end point of 0.1 M NH3FeSO4 reached.

End Point and Calculation
I. Absorbance Method:
1) Absorbance reading will show significant increases, until some points, then the reading will decrease.
2) When this absorbance reading suddenly jump from the increasing trend into decreasing trend, the end point of the titration has reached.
3) Continue the NH3FeSO4 solution addition by another 2 or 3 cc volume to get the smooth curve and/or representative data for accurate interpolation of the end point volume.
4) Draw the absorbance curve versus titrant volume addition then determine the end point volume by this curve or using all absorbance and NH3FeSO4 volume addition through Lagrance interpolation formula to get the end point volume.
5) Calculate the concentration or active matter of Tetra Hydroxy Ethyl Di Sulphate Di Natrium (THES-2Na) using the formula below:

$$\text{THES 2Na content} = (V\ ep \times M\ NH3FeSO4 \times MW\ THES\ 2Na \times 3.9)/(V\ sample \times sample\ SG \times 1{,}000)$$

where:
V ep: end point volume in cc
M NH3FeSO4: molarity NH3FeSO4: 0.1 M
BM THES 2Na: molecule weight THES 2Na: 330
V sample: sample volume of tested chelant in cc

EXAMPLE

Take 1.0 cc of 35% Tetra Hidroksi Etil Di Sulfat Di Natrium (THES-2Na) solution as sample, density of 1.1 g/cc. Then add on Na-SLES, titrate with 0.1 M NH3FeSO4; the absorbance record shown in the Table 1 below:

TABLE 1

| No | ml titer NH3FeSO4 | Absorbance 450 nm |
|---|---|---|
| 1 | 0 | 0.001 |
| 2 | 1 | 0.011 |
| 3 | 2 | 0.025 |
| 4 | 3 | 0.042 |
| 5 | 4 | 0.156 |
| 6 | 5 | 0.241 |
| 7 | 6 | 0.32 |
| 8 | 7 | 0.355 |
| 9 | 8 | 0.385 |
| 10 | 9 | 0.397 |
| 11 | 10 | 0.404 |
| 12 | 11 | 0.41 |
| 13 | 12 | 0.411 |
| 14 | 13 | 0.414 |
| 15 | 14 | 0.413 |
| 16 | 15 | 0.412 |

From Table 1 above, the absorbance curve versus volume NH3FeSO4 trend is shown in FIG. 1.

From FIG. 1, the end point volume is 3.5 ml, Molarity NH3FeSO4 is 0.1 M, MW THES-2Na is 330 and sample volume of 1.0 cc with SG 1.1:

THES-2Na concentration=3.2 cc×0.1 M×330×3.9/(1.0×1.15×1,000)=0.358=35.8% of chelating agent.

Characteristics of this New Invention Substances

These substances of this new invention are preferred to have the characteristics as below:

a. Tetra Hydroxy Ethyl Di Sulphate (THES)

| | |
|---|---|
| Molecular weight | 286 |
| Crystal density (g/cuCm) | 1.865 |
| Solubility @ 25° C. (%) | 48.0 |
| pH of 30% solution | <0.5 |
| Melting point (° C.) | 218 |
| Boiling point (° C.) | >400 |
| Colour | Off white |
| Crystal charactheristic | Hygroscopic | b. Tetra Hydroxy Ethyl Di Sulphate Di Natrium

| | |
|---|---|
| Molecular weight | 330 |
| Crystal density (g/cuCm) | 2.215 |
| Solubility @ 25° C. (%) | 31.5 |
| pH of 30% solution | 0.5-1.5 |
| Melting point (° C.) | 287 |
| Boiling point (° C.) | >400 |
| Colour | Transparance |
| Crystal charactheristic | Slightly hygroscopic | c. Tetra Hydroxy Butyl 1,2,3,4 Tetra Sulphate

| | |
|---|---|
| Molecular weight | 506 |
| Crystal density (g/cuCm) | 2.28 |
| Solubility @ 25° C. (%) | 39.6 |
| pH of 30% solution | <0.0 |
| Melting point (° C.) | 242 |
| Boiling point (° C.) | >400 |
| Colour | White brownies |
| Crystal charactheristic | Very hygroscopic | d. Tetra Hydroxy Butyl 1,2,3,4 Tetra Sulphate Tetra Natrium

| | |
|---|---|
| Molecular weight | 594 |
| Crystal density (g/cuCm) | 2.978 |
| Solubility @ 25° C. (%) | 27.3 |
| pH of 30% solution | 0.0-1.0 |
| Melting point (° C.) | 288 |
| Boiling point (° C.) | >400 |
| Colour | Transparance |
| Crystal charactheristic | hygroscopic | e. Tri Hydroxy Isobutyl 1,2,3-Tri Sulphate

| | |
|---|---|
| Molecular weight | 393 |
| Crystal density (g/cuCm) | 1.97 |
| Solubility @ 25° C. (%) | 56.7 |
| pH of 30% solution | <0.0 |
| Melting point (° C.) | 191 |
| Boiling point (° C.) | >400 |
| Colour | White brownies |
| Crystal charactheristic | Very hygroscopic | f. Tri Hydroxy Isobutyl 1,2,3-Tri Sulphate Tri Natrium

| | |
|---|---|
| Molecular weight | 459 |
| Crystal density (g/cuCm) | 2.35 |
| Solubility @ 25° C. (%) | 36.2 |
| pH of 30% solution | 0.0-1.0 |
| Melting point (° C.) | 242 |
| Boiling point (° C.) | >400 |
| Colour | Off white |
| Crystal charactheristic | hygroscopic | g. Tetra Hydroxy Isoamyl 1,2,3,4-Tetra Sulphate

| | |
|---|---|
| Molecular weight | 519 |
| Crystal density (g/cuCm) | 2.07 |
| Solubility @ 25° C. (%) | 61.2 |
| pH of 30% solution | <0 |
| Melting point (° C.) | 211 |
| Boiling point (° C.) | >400 |
| Colour | White brownies |
| Crystal charactheristic | Very hygroscopic | h. Tetra Hydroxy Isoamyl 1,2,3,4-Tetra Sulphate Tetra Natrium.

| | |
|---|---|
| Molecular weight | 607 |
| Crystal density (g/cuCm) | 2.63 |
| Solubility @ 25° C. (%) | 40.1 |
| pH of 30% solution | 0.0-0.5 |
| Melting point (° C.) | 247 |
| Boiling point (° C.) | >400 |
| Colour | Off white |
| Crystal charactheristic | hygroscopic | i. Asam Etil Heksa Sulfat (EHS)

| | |
|---|---|
| Molecular weight | 606 |
| Crystal density (g/cuCm) | 1.87 |
| Solubility @ 25° C. (%) | 48% |
| pH of 30% solution | 0.0 |
| Melting point (° C.) | >210° C. |
| Boiling point (° C.) | >400° C. |
| Colour | Off white |
| Crystal charactheristic | hygroscopic | j. Etil Heksa Sulfat-Heksa Natrium (EHS-6Na)

| | |
|---|---|
| Molecular weight | 738 |
| Crystal density (g/cuCm) | 1.87 |
| Solubility @ 25° C. (%) | 48% |
| pH of 30% solution | 0.0-0.5 |
| Melting point (° C.) | >210° C. |
| Boiling point (° C.) | >400° C. |
| Colour | Off white |
| Crystal charactheristic | hygroscopic |

Ability to Enlarge the Simple Cell Membrane

The substances of this invention were found to have the ability to modify the cell membrane or organic membrane by means enlarging/loosening membrane porosity significantly. By not totally theoretically supported, it was postulated due to the sulphate group electronegativity in the said substances as the chelating agent will loosen the hydroxy-hydroxy bound of a peptidoglycan or hydroxy-ammine bound of a protein that compose the membrane cell nor organic membrane. The ability of these substances to enlarge/loosen the membrane porosity were proven by opening/enlarging the microorganism cell membrane, ie: bacteri, algae, fungi, virus, etc with such concentration level that works on the cell wall membrane modification from the semi permeable into more permeable until it is possible to insert another ligands inside the microorganism or the cell wall membrane becomes totally permeable that result on the microorganism death or its latent position. It has been thought that the said mechanism works for all microorganism that has the cell membrane. The said ability to modify the simple cell membrane permeability will be shown by the mechanism and testing data below:

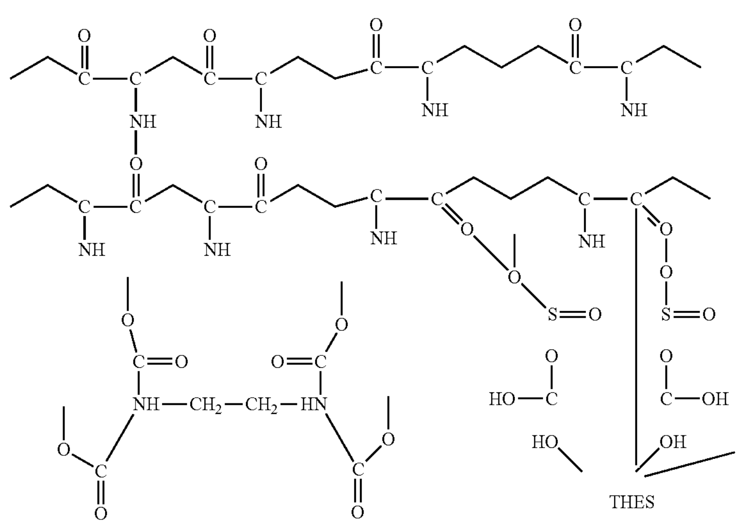

EDTA THES

Method:

The ability of Tetra Hydroxy Ethyl Di Sulphate-Di Natrium (THES) as a Sulphate chelating agent to open/loosen the cell membrane was tested against two types of bacterias, ie: *Staphylococcus aerus* (gram positive) that has two cell membrane (the outer membrane as the outer cell wall and the inner membrane) and E. Colli (gram negative) that has three cell membranes. First, the Minimum Inhibitory Concentration (MIC) of each bacterias was determined, then the bacteria membrane alteration after contacting with THES were observed by Electron Microscope (TEM and SEM) with the THES concentration range below and above MIC. Antibacterial activity was tested using disc-diffusion method by checking the clear zone from the paper disc inhibition that contains THES. The growth curve were made by means examining the bacterial culture on the broth media.

Materials and Equipments:

Materials

Difco brand nutrient broth, aquadistilata, THES (tetra hydroxy ethyl di sulphate di natrium) as the tested substance, glutaraldehyde, paraformaldehyde, albumin serum bovin (BSA), buffer phosphate pH 7, NaCl 0.9%, white LR resin, blue toluidine, Natrium citrate trihydrate, NaOH 0.1N, uranil acetate, lead nitrate ($Pb(NO_3)_2$), parafin, transparan capsule, glass cutter, grid, collodion, gold powder.

Equipments:

Incubator, autoclave, petri dish, ose, spectrophotometer (Bausch&Lomb), vibrating incubator, glassware, ultra mikrotom, knife maker, visible microscope, grid pad, transmission electron microscope (Philips), scanning electron microscope (Hitachi).

TABLE 2

Result of Biocide effication plate test of Tetra Hydroxy Ethyl Di Sulphate-Di Natrium (THES-Di Natrium)

| No | Biocide dosing | Total Plate Count (Colony/ml) | Killing efficiency |
|---|---|---|---|
|  | Total Plate Count Microorganism |  |  |
| 1 | Blanco/Control | 2400 | 0 |
| 2 | 0.05% THES-di Natrium | 132 | 94.5 |
| 3 | 0.1% THES-di Natrium | 115 | 95.2 |
| 4 | 0.5% THES-di Natrium | 101 | 95.8 |
| 5 | 1.0% THES-di Natrium | 80 | 96.7 |
|  | *E. Coli* |  |  |
| 1 | Blanco | 3900 | 0 |
| 2 | 0.025% THES-di Natrium | 2010 | 48.5 |
| 3 | 0.05% THES-di Natrium | 1150 | 70.5 |
| 4 | 0.1% THES-di Natrium | 1050 | 73.1 |
| 5 | 0.5% THES-di Natrium | 970 | 75.1 |
| 6 | 1.0% THES-di Natrium | 720 | 81.5 |
| 7 | 5.0% THES-di Natrium | 630 | 83.8 |
|  | *Staphylococcus Aerus* |  |  |
| 1 | Blanco | 980 | 0 |
| 2 | 0.025% THES-di Natrium | 296 | 69.8 |

Test on Microorganism:

*Staphylococcus aerus* ATCC 6538, *Escherichia coli* ATCC 9637 were supplied from Chemotherapy Laboratory of Pharmaceutical Department, Bandung Institute of Technology (ITB).

Method:
1. Bacteria preparation
    The testing bacterias were growth on the aqueous medium and incubated for 24 hours at 37° C.
2. Tested Biocide preparation
    The tested Biocide was diluted in distillate water at various gradually decreased concentration. This gradual concentration variation is necessary to determine MIC (Minimum Inhibitory Concentration) and the bacteriostatic/bactericidal properties of the tested Biocide.
3. Determination of Killing method (bacteriostatic and bactericidal properties)
    The testing was done on the aqueous medium contains the tested substance with the concentration 5, 10 and 20%. The turbidity of the cultured medium then will be measured every 30 minutes until 270 minutes with spectrophotometer.
4. Preparation of microbe cells for electron microscope examination
    *Staphylococcus aereus* and *Escherichia coli* were growth on the aqueous medium within 24 hours, then mixed with tetra hydroxy ethyl di sulphate di sodium (THES) with the final concentration 0.6; 5 and 10%. This system mixtures then was placed under vibrating incubator for several hours. Microbe cells then were separated and washed, first with NaCl 0.9% then with distilled water. Cells then were utilized for the preparation of electron microscope testing.
5. Preparation for Scanning Electron Microscope (SEM) examination
    Bacteria cells were suspended into 4% collodion. The said suspensions then were fixed on some metal disc and were coated with the gold powder. Then were examined with electron microscope and pictured.
6. Preparation for Transmittance Electron Microscope (TEM) examination
    a) The prepared microbes in (5) were fixed into a mixture of formaldehyde 2% and glutaraldehyde 0.5% for 2 hours at 4° C.
    b) The above mixtures then was three times washed with pH 7 phosphate buffer, then were diluted into bovin serum albumin (BSA) 1/5 for embedded preparation, while leave glutaraldehyde hardening at room temperature.
    c) After leaving dehydrated in alcohol, the white LR resin then will be infiltrated.
    d) Embedded process were done at white LR resin following by polymerization process at 60° C. for 48 hours time. The polymerization product as hardened capsules then are ready to be sliced.
    e) Making of semi thin and ultra thin slices.
        Slices of microbe sample were made by utilizing automatic ultra microtom. To get the precised and accurate slices of sample, semi thin slice were made and coloured with blue toluidine then were examined under the visible microscope. When the right slices were obtained, ultra thin slices were prepared and were made contrast with uranil acetate and lead citrate. The dried ultra thin slices then can be examined with Transmittance Electron Microscope.

Testing Results

Minimum Inhibitory Concentration (MIC)

MIC of tetra hydroxy ethyl di sulphate di natrium against *E. coli* and *S. aureus* are shown in Table 3.

TABLE 3

Antibacterial activity of Tetra Hydroxy Ethyl
Di Sulphate-Di Natrium (THES-Di Natrium)

| No | Microorganisme | Minimum Inhibitory Concentration (MIC) (%) |
|---|---|---|
| | Gram Positive Bacteria | |
| 1 | *Bacillus Subtilis* ATCC 6633 | 0.234 |
| 2 | *Staphylococcus Aerus* ATCC 6538 | 0.234 |
| 3 | *Staphylococcus Epidermidis* ATCC 12228 | 0.234 |
| | Gram Negative Bacteria | |
| 1 | *Acinetobacter Anitratus* | 0.115 |
| 2 | *Escherichia Coli* ATCC 25922 | 0.234 |
| 3 | *Pseudomonas Aeruginosa* ATCC 27853 | 0.115 |
| 4 | *Klebsiella Pneumoniae* | 0.234 |
| 5 | *Salmonella Typhii* | 0.115 |
| | Fungi | |
| 1 | *Aspergillus Niger* | 0.937 |
| 2 | *Candida Albicans* | 0.469 |

The test done on the pH range of 7-7.5 with the sample of Tetra Hydroxy Ethyl Di Sulphate-Di Natrium (THES-Di Natrium) 30% in aqueous solution.

From the transversal section (TEM) of *Staphylococcus aerus* cell, can be observed between normal cell that still contains cytoplasm and other organic substances (dark sight) and the partly empty cells that has already lost its cytoplasm liquid due to lysis out of cell wall membrane (transparent sight), in fact the *E. Colli* cell that has more layers cell wall membranes also experienced the said internal cell liquid lysis out of its cell wall membrane layers, although the MIC of *E. Colli* cell was slightly higher than *Staphylococcus aerus* cell.

From the outer surface of bacteria's cell wall observation through Scanning Electron Microscope (SEM), it was shown that the outer cell wall membrane of bacteria looked wrinkled/corrugated due to the wider cell wall surface compared to normal cell wall for both *Staphylococcus aerus* nor *E. Colli*.

The invention claimed is:

1. A compound of formula I below:

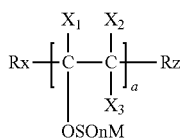

wherein $X_1$ and $X_2$, are selected independently from hydroxy, halide, sulphite, sulphate, sulphonate, phosphorus derivatives, and nitrogen derivatives,
$X_3$ is sulphonate or sulphate,
Rx, Rz are selected independently from hydrogen, hydroxy, halide, alkyl $C_{1-20}$, alkylene $C_{1-20}$, alkyl alcohol $C_{1-20}$, aryl, cycloalkyl, sulphite, sulphate, sulphonate, phosphorus derivatives, and nitrogen derivatives,
M is selected from hydrogen, group I cation, group II cation, and transition group cations that are pharmaceutically acceptable,
n is an integer from 0-3,
a is an integer.

2. The compound according to claim 1, whereas the compound is selected from
Tetra Hydroxy Ethyl Di Sulphate,
Tetra Hydroxy Butyl 1,2,3,4 Tetra Sulphate,
Tri Hydroxy Isobutyl 1,3,4-Tri Sulphate,
Tetra Hydroxy Isoamyl 1,3,4,5-Tetra Sulphate, and
Ethyl hexa sulphate acid.

3. The compound according to claim 1, whereas M is natrium.

4. The compound according to claim 1, whereas the compound is selected from
Tetra Hydroxy Ethyl Di Sulphate Di Natrium,
Tetra Hydroxy Butyl 1,2,3,4 Tetra Sulphate Tetra Natrium,
Tri Hydroxy Isobutyl 1,3,4-Tri Sulphate Tri Natrium,
Tetra Hydroxy Isoamyl 1,3,4,5-TetraSulphate Tetra Natrium, and
Ethyl Hexa Sulphate-Hexa Natrium (EHS-6Na).

5. The compound according to claim 1, wherein the compound is a chelating agent.

6. The compound according to claim 1, where the compound increases the permeability of a microbial membrane.

7. The compound according to claim 1, wherein the compound is a biocide.

8. A method of synthesis of a compound according to formula I, the method comprising:
reacting at least one of sulphuric acid ($H_2SO_4$,), sulphonic acid ($H_2SO_3$), and sulfur dioxide ($SO_2$), with at least one of formaldehyde, acetaldehyde, formic acid, acetic acid, and oxalic acid to form an intermediate; and
reacting the intermediate with at least one of a hydrogen, halide, phosphorous derivative, nitrogen derivative, sulphonate, and sulphate to obtain the compound of Formula I

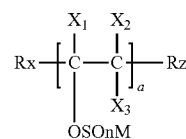

wherein $X_1$ and $X_2$ are selected independently from hydrogen, hydroxy, halide, sulphite, sulphate, sulphonate, phosphorus derivatives, and nitrogen derivatives,
$X_3$ is sulphonate or sulphate,
Rx, Rz are selected independently from hydrogen, hydroxy, halide, alkyl $C_{1-20}$, alkylene $C_{1-20}$, alkyl alcohol $C_{1-20}$, aryl, cycloalkyl, sulphite, sulphate, sulphonate, phosphorus derivatives, and nitrogen derivatives,
M is selected from hydrogen, group I cation, group II cation, and transition group cations that are pharmaceutically acceptable,
n is an integer from 0-3,
a is an integer.

9. The method of claim 8 wherein the at least one of sulphuric acid ($H_2SO_4$,), sulphonic acid ($H_2SO_3$), and sulfur dioxide ($SO_2$), is reacted with at least one of formaldehyde, acetaldehyde, formic acid, asetic acid, and oxalic acid.

10. A method to lyse a hydroxy-hydroxy bond in a peptidoglycan or an hydroxyl-amide bound on protein that compose a cell wall membrane by a compound of formula I, wherein the method comprises enlarging, by the compound of formula I, the membrane porosity of both of sides of the membrane,

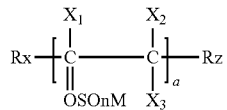

wherein $X_1$, $X_2$, $X_3$, are selected independently from hydrogen, hydroxy, halide, sulphite, sulphate, sulphonate, phosphorus derivatives, and nitrogen derivatives, Rx, Rz are selected independently from hydrogen, hydroxy, halide, alkyl $C_{1-20}$, alkylene $C_{1-20}$, alkyl alcohol $C_{1-20}$, aryl, cycloalkyl, sulphite, sulphate, sulphonate, phosphorus derivatives, and nitrogen derivatives, M is selected from hydrogen, group I cation, group II cation, and transition group cations that are pharmaceutically acceptable, n is an integer from 0-3, a is an integer.

* * * * *